United States Patent [19]
Schwartz

[11] Patent Number: 5,846,200
[45] Date of Patent: Dec. 8, 1998

[54] ULTRASONIC DIAGNOSTIC IMAGING SYSTEM FOR ANALYSIS OF LEFT VENTRICULAR FUNCTION

[75] Inventor: Gary Allen Schwartz, Seattle, Wash.

[73] Assignee: Advanced Technology Laboratories, Inc., Bothell, Wash.

[21] Appl. No.: 747,100

[22] Filed: Nov. 8, 1996

[51] Int. Cl.$^6$ .................................................. A61B 8/00
[52] U.S. Cl. ........................................ 600/443; 128/916
[58] Field of Search .................................. 600/437, 443, 600/447, 455; 128/916; 382/128

[56] References Cited

U.S. PATENT DOCUMENTS

| | | | |
|---|---|---|---|
| 4,341,120 | 7/1982 | Anderson | 73/618 |
| 5,056,526 | 10/1991 | Khalil | 128/692 |
| 5,181,514 | 1/1993 | Solomon et al. | 128/660.09 |
| 5,295,486 | 3/1994 | Wollschlager et al. | 128/661.01 |
| 5,302,372 | 4/1994 | Lin et al. | 424/9 |
| 5,322,067 | 6/1994 | Prater et al. | 128/660.07 |
| 5,379,769 | 1/1995 | Ito et al. | 128/916 |
| 5,415,171 | 5/1995 | Goh et al. | 128/660.07 |
| 5,435,310 | 7/1995 | Sheehan et al. | 600/437 |
| 5,450,850 | 9/1995 | Iinuma | 128/661.09 |
| 5,458,126 | 10/1995 | Cline et al. | 128/653.1 |
| 5,460,181 | 10/1995 | Seyed-Bolorforosh | 128/916 |
| 5,474,073 | 12/1995 | Schwartz et al. | 128/661.1 |
| 5,485,842 | 1/1996 | Quistgaard | 128/66.07 |
| 5,487,388 | 1/1996 | Rello et al. | 128/660.09 |
| 5,570,430 | 10/1996 | Sheehan et al. | 382/128 |

OTHER PUBLICATIONS

"A method for three–dimensional ultrasonic imaging of the heart in vivo", H. McCann et al, *Dynamic Card. Imag.* v 1, No. 2, pp. 97–109 (1987).

*Primary Examiner*—William E. Kamm
*Assistant Examiner*—Maulia Patel
*Attorney, Agent, or Firm*—W. Brinton Yorks, Jr.

[57] ABSTRACT

An ultrasonic diagnostic imaging system is provided for measuring the volume of a chamber of the heart or other organ or vessel. An ultrasonic transducer probe is used to scan the chamber with a plurality of spatially distinct scan planes. The pixels of the chamber volume of each scan plane are aggregated to provide a measure of the volume. In a preferred embodiment the chamber volume pixels are developed from Doppler signals from the fluid within the chamber, and are related to voxels within the chamber by weighting pixels in the scan planes in accordance with the voxel sampling afforded by the inter-plane separation.

24 Claims, 6 Drawing Sheets

ULTRASONIC DIAGNOSTIC IMAGING SYSTEM FOR ANALYSIS OF LEFT VENTRICULAR FUNCTION

This invention relates to ultrasonic diagnosis and imaging of the cardiovascular system of the body and, in particular, to ultrasonic analysis of left ventricular function of the heart.

The heart is an organ for which a great variety of diagnostic tools have been created or are under development, both invasive and noninvasive. The coronary arteries, heart valves, and the myocardial muscle itself all are subject to scrutiny by many modalities of equipment in the diagnosis and treatment of heart disease. Among the many parameters of heart performance that are analyzed are those relating to the capability of the heart to pump blood. Since the left ventricle is the chamber of the heart which pumps oxygenated blood into the aorta and thence to all other regions of the body, left ventricular assessment is of significant diagnostic interest. Parameters and measurements which have been developed to diagnose the left ventricle include left ventricular volume, mass, and ejection fraction. The ejection fraction is a measure of the volume of blood pumped with each heartbeat and is calculated as the ratio of the stroke volume of the left ventricle over end-diastolic volume of the left ventricle. The left ventricular ejection fraction is considered to be one of the most sensitive values of left ventricular function and is useful for detecting the onset of congestive heart failure.

A number of diagnostic modalities have been developed for assessing left ventricular function, including echocardiography, radionuclide ventriculography, selective angiocardiography, rapid CT, and MRI. Echocardiography is often the modality first used, due to its portability, safety, and ease of use. However, echocardiography has inherent limitations, including limitations of image plane orientation imposed by intercostal access and other thoracic anatomy, and geometric assumptions used to define endocardial and epicardial contours. When echocardiography does not serve the purpose, radionuclide ventriculography is generally the modality employed for diagnosis. In this modality a radioactive tracer is injected into the bloodstream, emitting radiation as it passes through the body. A gamma camera directed at the heart accumulates emitted radioactive particles in the image plane of the camera on a spatial basis, and the number of particles accumulated and their rate of accumulation can be displayed numerically or imaged and used in the assessment of left ventricular systolic and diastolic performance, from which an ejection fraction can be determined. It would be desirable to improve the ability to measure the ejection fraction through noninvasive echocardiograpy, so that the resort to invasive, radionuclide techniques is avoided.

In accordance with the principles of the present invention, an ultrasonic diagnostic imaging system is provided which is capable of assessing cardiac performance, including left ventricular function. A chamber of the heart is ultrasonically scanned to obtain a plurality of spatially distinct two dimensional images of the heart chamber. The pixels within the scan planes are related to voxel locations within the chamber and integrated to determine the volume of the chamber. In a preferred embodiment the relation of image pixels to voxels in the heart chamber is done by a mapping technique, wherein pixels are weighted in proportion to the sampling of the chamber volume effected by the multiple scan planes.

To calculate ejection fraction, two volume measurements of the heart chamber are made, at the end diastolic and peak systolic heart phases. The two volume measurements are then used to calculate the ejection fraction of the chamber.

Figure 1:
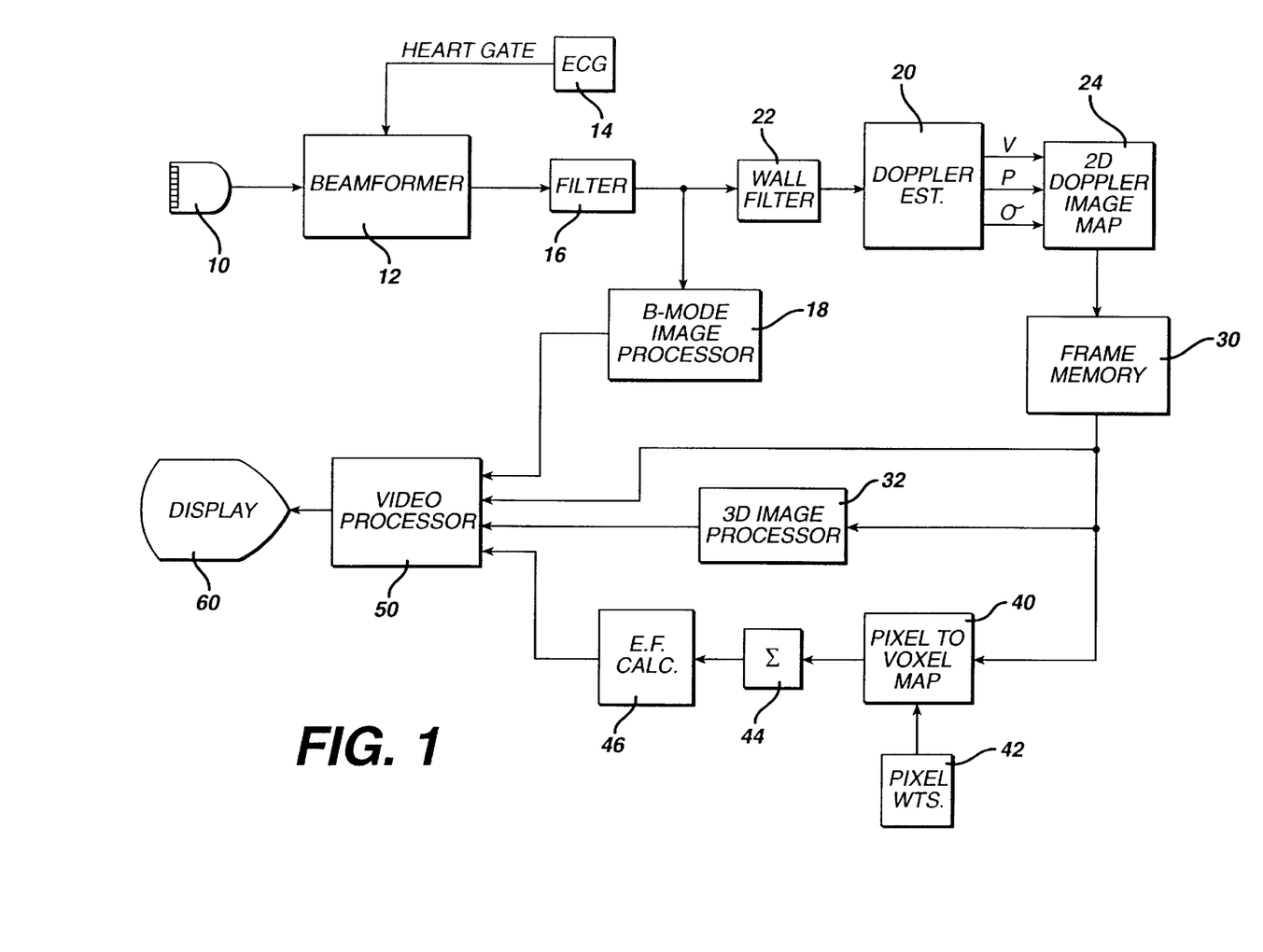
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. An ultrasonic transducer probe 10 preferably including a phased array transducer transmits ultrasonic waves into the body of a patient and receives echoes from organs and tissue within the body. In a preferred embodiment ultrasonic transmission is synchronized or gated to selected phases of the heart cycle by use of an ECG heart gate waveform produced by an ECG detector 14. Echoes received by individual transducer elements of the probe are formed into coherent beams of echoes by a beamformer 12, which also controls the phasing of transmission by the transducer elements to steer and focus the beams. The received echoes are filtered by a bandpass filter 16 matched to the desired echo passband, then processed to form B-mode or Doppler signals. A B-mode image processor 18 detects and processes echo signals to form two dimensional (2D) images of the structure of the body. Echoes which are to be Doppler processed are first processed by a wall filter 22 to eliminate high amplitude, low frequency echoes returned from structures in the body such as the heart wall. The remaining flow signals emanating from bloodflow are then processed by a Doppler estimator 20 to produce Doppler estimates of bloodflow velocity (v), Doppler power (P), or variance ($\sigma$). The selected bloodflow parameter or parameters are then mapped into a 2D image by a 2D Doppler image mapping processor 24 and the resultant image is stored in an image frame memory 30.

A plurality of frames acquired from different spatial locations of a volumetric region of the body are stored in the frame memory 30 for further processing in a number of ways. One type of processing which may be performed is 3D image processing by a 3D image processor 32, which operates on the image frames to produce 3D renderings as described in U.S. Pat. Nos. 5,474,073 and 5,485,842. In accordance with the principles of the present invention, the pixels of a plurality of spatially distinct images of the bloodflow of a region of the body such as the left ventricle are mapped to voxel locations in the region by a pixel to voxel mapping processor 40. The pixels are weighted in relation to the sampling density of the heart chamber effected by the pixels in the images, and the weighted pixels are summed or integrated at 44 to produce a value which is a measure of the volume of the blood pool of the chamber. When two such values are produced for the blood pool of the left ventricle, one at peak systole and another at end diastole, the two values can be used to calculate left ventricular ejection fraction by an ejection fraction calculator 46.

The outputs of the various processors are coupled to a video processor 50. The video processor processes the various image signals for display on a display 60. The video processor can produce 2D B-mode images from signals provided by the B-mode image processor 18, and can combine 2D B-mode images with corresponding Doppler images from the frame memory 30 to produce colorflow Doppler or Doppler power images. The video processor can produce 3D images for display from signals provided by the 3D image processor 32, and can display ejection fraction calculations produced by the ejection fraction calculator 46.

Figure 2:
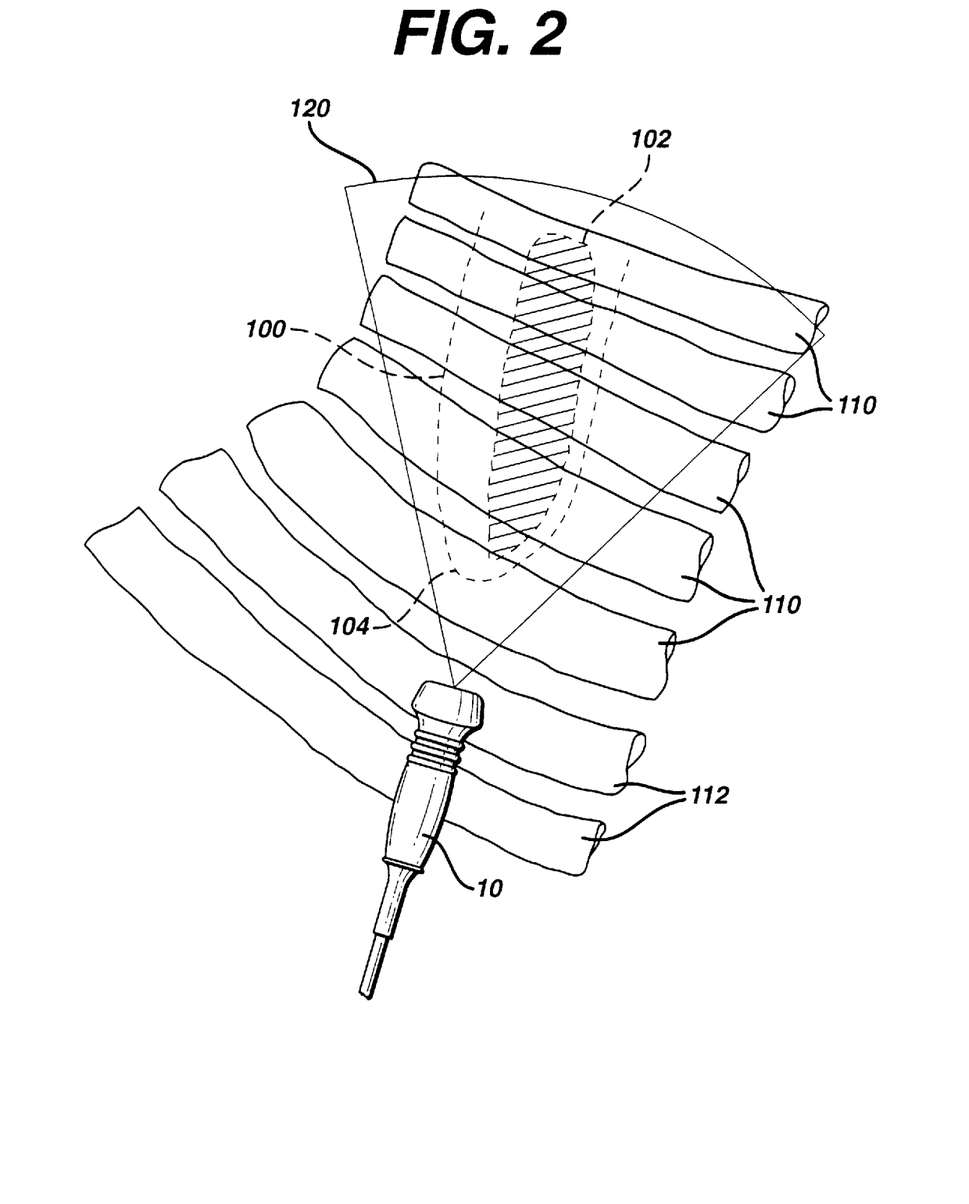
FIG. 2 illustrates apical ultrasonic scanning of the left ventricle of the heart.

Turning now to FIG. 2, a technique for ultrasonically scanning the left ventricle of the heart is shown. The heart 100, shown in partial outline behind the rib cage 110,112 is located behind the left side of the rib cage. Outlined within the heart and cross-hatched is the left ventricle 102 of the heart 100. The left ventricle can be accessed for ultrasonic imaging by scanning the heart from between the ribs 110,112 for adult patients and, for some pediatric patients, by scanning upward from below the lowest rib 112. The probe 10 scans the heart from the heart apex 104 as indicated by the outline 120 of the image sector scanned by the probe 10. As FIG. 2 illustrates, the left ventricle 102 can be fully encompasses and scanned by a sector scan directed from between the rib cage 110,112.

Figure 3:
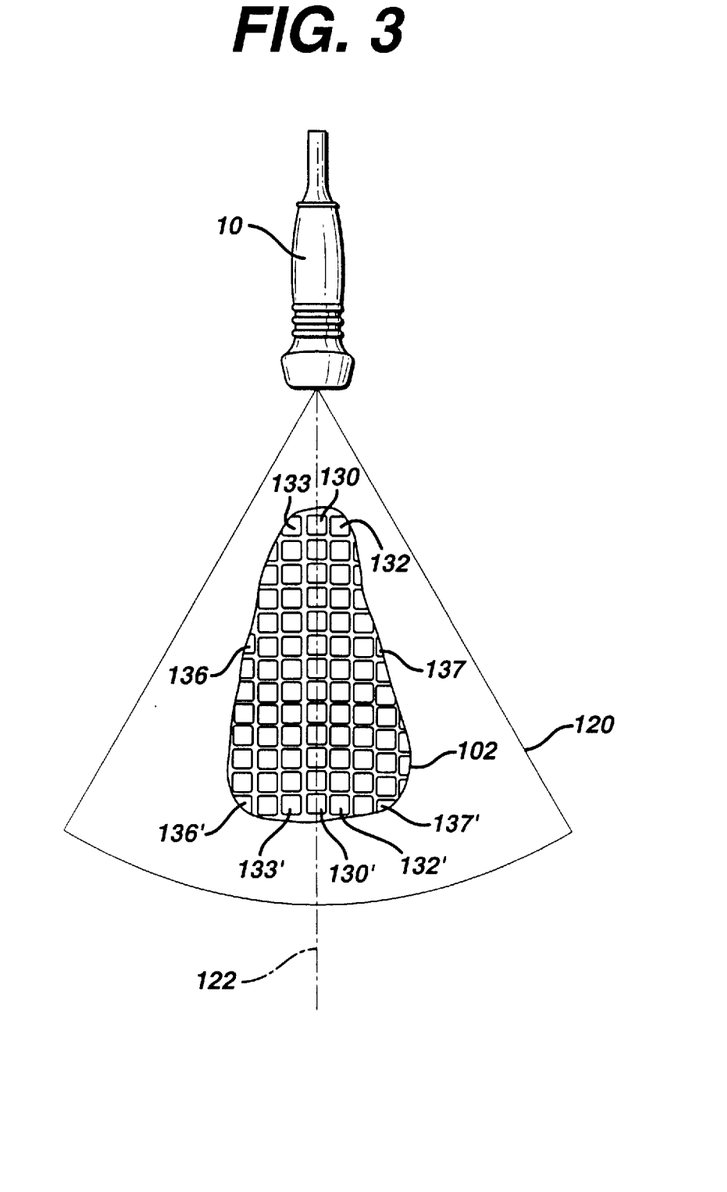
FIG. 3 illustrates an ultrasonic image acquired from the apical scanning of FIG. 1.
Figure 4:
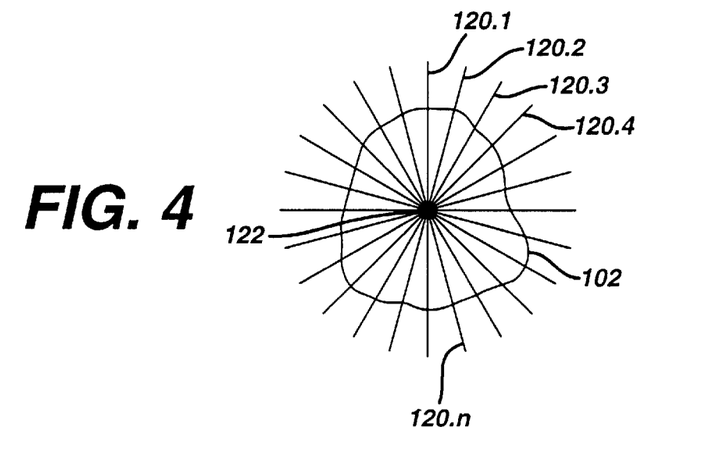
FIG. 4 illustrates image planes acquired through rotation of an ultrasonic transducer about its central axis.

In order to determine the volume of a chamber of the heart, a number of spatially distinct scan planes of the chamber are acquired. A number of acquisition techniques are possible. One scan plane of the left ventricle 102 chamber is shown in FIG. 3, located about a centerline 122. The transducer probe 10 may be turned about this centerline to acquire a number of angularly disposed scan planes of the left ventricle with a common center axis. A group of scan planes acquired in this manner are shown edge-on in FIG. 4. Preferably, the transducer is automatically turned about a centerline normal to the center of the transducer as can be performed by the transducer probe mechanism described in McCann et al., "Multidimensional Ultrasonic Imaging for Cardiology", *Proceedings of the IEEE,* vol. 76, no. 6, September 1988 at 1063–73. FIG. 4 shows a number of ultrasonic scan planes with a common centerline 122 through the left ventricle 102 as scan planes 120.1, 120.2, 120.3, 120.4 . . . 120.n. In a preferred embodiment each successive scan plane is angularly oriented with respect to adjacent scan planes by about 4° of rotation.

One of the scan planes of FIG. 4 is depicted in FIG. 3, containing pixels 130–137' of the blood pool 102 of the left ventricle. In a preferred embodiment these pixels are produced by Doppler power imaging of the blood pool of the left ventricle, which advantageously provides highly sensitive, segmented images of the blood pool. The image plane pixels are mapped to the voxels of the left ventricle blood pool, and the degree to which they sample the blood pool is noted. In FIG. 4 it is seen that the intersection of all of the scan planes at their common centerline 122 (the point of intersection in this drawing) results in relative oversampling of voxels in this region of the left ventricle, as each scan plane contains pixels from along the centerline 122. However, at the periphery of the chamber the voxels are relatively undersampled, due to the relatively sizable angular spacing between adjacent scan planes.

Figure 4A:
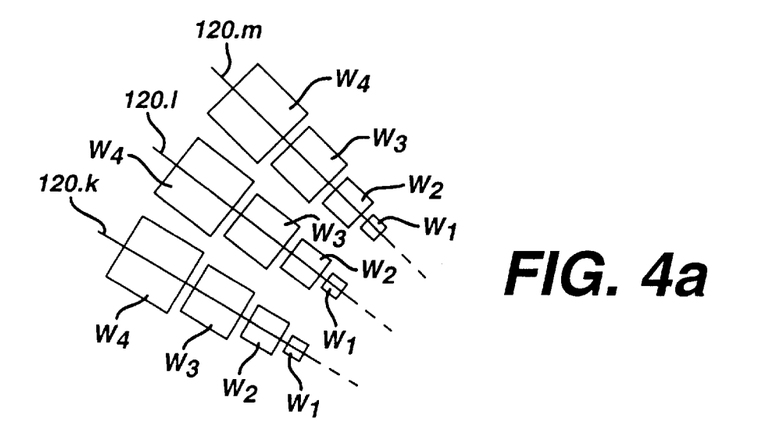
FIG. 4a illustrates the voxel weighting of pixels in an image plane in accordance with interplane spacing.

In consideration of the variation in scan plane spacing and hence the relative degree of voxel sampling, the pixels in the blood pool images are weighted accordingly. Such weighting for a plurality of angularly disposed scan planes 120.k, 120.l, and 120.m is illustrated in exaggerated form in FIG. 4*a*, where the scan planes are again shown edge-on. In this drawing the pixels which are relatively closely spaced to adjacent scan planes are weighted by a relatively small weighting factor $w_1$, illustrated by the small box $w_1$. More widely separated pixels outwardly spaced from the inner pixels of the scan planes are weighted by increasing weights as shown by the boxes of increasing sizes $w_2$ and $w_3$. At the periphery of the scan planes, where the plane to plane separation is the greatest and hence the blood pool is most sparsely sampled, the pixels are given the greatest weights as indicated by the largest boxes $w_4$. In the scan plane 120 of FIG. 3, this weighting scheme results in the pixels (shown as small boxes) located along the centerline of image overlap from pixel 130 through pixel 130' being the most lightly weighted; the next outward rows of pixels, from pixel 133 to pixel 133' and from pixel 132 to pixel 132' are more greatly weighted; and the more outwardly rows of pixels from pixel 136 to pixel 136' and from pixel 137 to pixel 137', are even more greatly weighted. Thus, the pixels of each plane 120.1 . . . 120.n are weighted in accordance with the density with which the voxels of the blood pool are sampled by the chosen inter-plane spacing.

After all the pixels of the scan planes are weighted the weighted pixels of the blood pool are integrated or summed as indicated at 44 to produce a measure of the volume of the blood pool.

Figure 7:
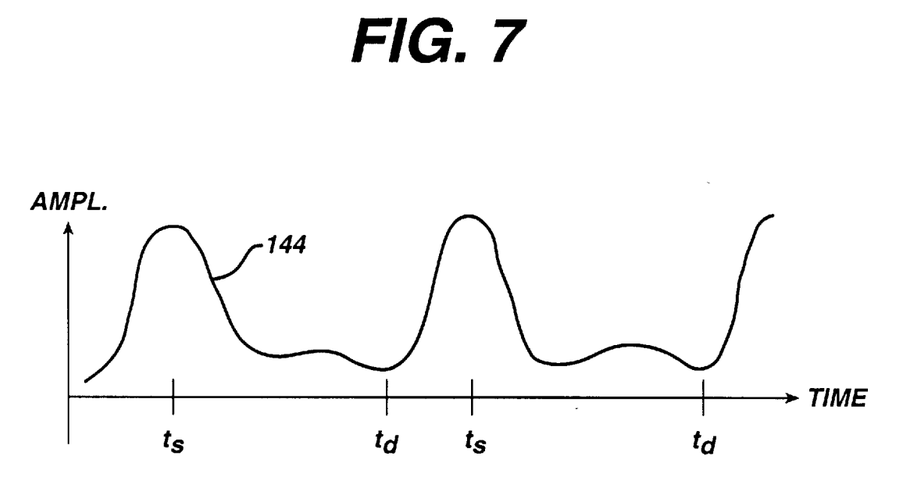
FIG. 7 illustrates the timing of peak systole and end diastole heart gating from an ECG waveform.

To compute the left ventricular ejection fraction, two measures of left ventricular volume are made, one at peak systole when the left ventricle is fully contracted, and the other at end diastole when the left ventricle is fully expanded. This means that two sets of spatially distinct scan planes must be acquired, one at peak systole and the other at end diastole. Scan plane acquisition at these times may be performed by heart gated scan plane acquisition using an ECG waveform as shown by the ECG waveform 144 of FIG. 7. Peak systole occurs each heart cycle at time $t_s$, and end diastole occurs at each time $t_d$. Scan planes are acquired at these two times, thereby permitting the acquisition of one scan plane for each scan plane set during each heart cycle. Depending upon the speed with which the scan plane can be rotated and the desired accuracy of the measurement, several scan planes could be rapidly acquired in succession at each time $t_s$ and $t_d$. Alternatively, several planes may be acquired at the same orientation at each gated interval and averaged on a frame to frame basis to produce a single scan plane of data with increased immunity to signal drop-out. At the end of this gated acquisition two sets of spatially distinct scan planes 120.1 . . . 120.n are stored in the frame memory 30 of FIG. 1, one set being acquired around times $t_s$ and the other set being acquired around times $t_d$. The blood pool pixels of each set of scan planes are then weighted in accordance with the chamber voxel sampling density and accumulated to produce one measure of left ventricular volume at peak systole and another measure of left ventricular volume and end diastole.

The two measures of left ventricular volume are then used to calculate left ventricular ejection fraction in accordance with the expression $$E.F. = \frac{Ved - Vps}{Ved}$$

where Ved is the chamber volume measured at end diastole and Vps is the chamber volume measured at peak systole. The calculated ejection fraction ratio is displayed to the user by means of the video processor 50 and the display 60.

Figure 5:
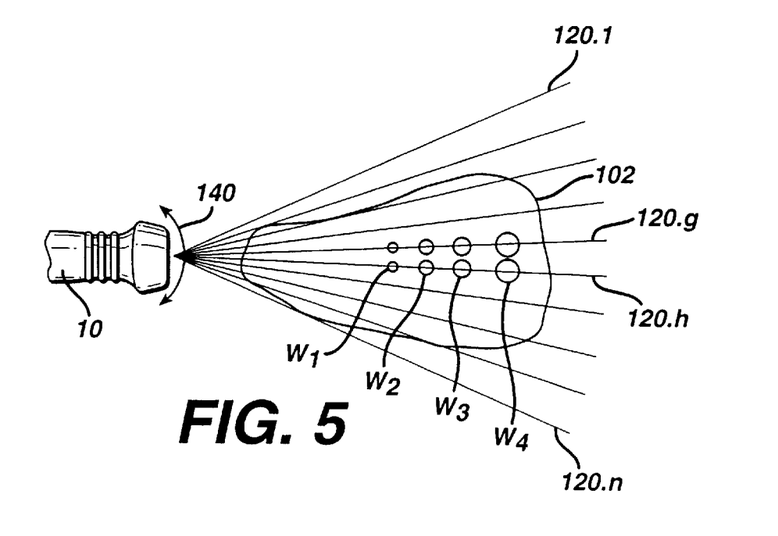
FIG. 5 illustrates ultrasonic scanning of the left ventricle by fanning an ultrasonic transducer through a plurality of angularly inclined scan planes.

Other techniques may be used to scan the heart chamber. In FIG. 5 for example the transducer probe 10 is rocked against the patient's body as indicated by the arrow 140 to fan the scan planes 120.1 . . . 120.n over the blood pool 102. As in FIG. 4, the scan planes 120.1 . . . 120.n in FIG. 5 are shown edge-on. As this drawing shows, the fan-shaped group of scan planes are again angularly disposed with respect to each other but in a different dimension than the preceding example, and are more widely separated at the right side of the drawing than at the left side. The blood pool voxels at the right side (further from the transducer probe) are more widely sampled than are the voxels at the left side (closer to the transducer probe). Hence, scan plane pixels to the right are more greatly weighted than are pixels to the left, as indicated by the circles $w_1$–$w_4$, which represent relative pixel weighting. As before, for ejection fraction measurements, two sets of scan planes are acquired, one set at end diastole and another set at peak systole. The weighted pixel values are integrated or summed to produce measures of chamber volume from each scan plane set, and the two measures used in the above expression to compute left ventricular ejection fraction. A device for fan scanning a transducer probe is described in U.S. Pat. No. 5,487,388.

Figure 6A:
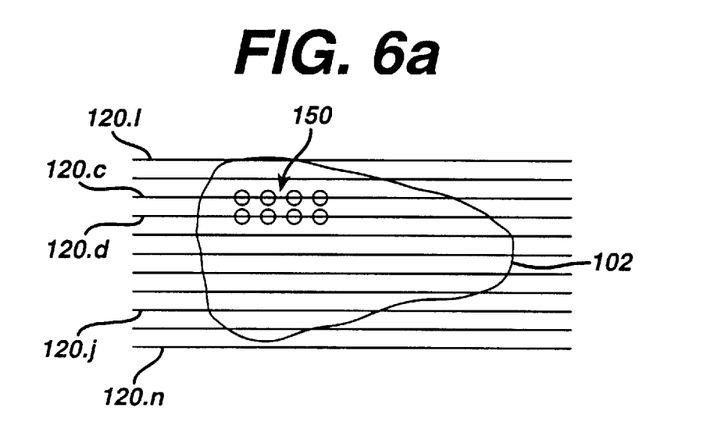
FIGS. 6a–6c illustrate ultrasonic scanning of the left ventricle with a plurality of parallel scan planes.

FIG. 6a illustrates a blood pool volume 102 which is scanned by a plurality of parallel scan planes 120.1 . . . 120.n. When the scan planes are oriented in parallel, uniform weighting can be used for the pixels in each scan plane, as the inter-plane spacing between adjacent scan planes is uniform. This is illustrated by the uniformly sized circles 150, representing uniform pixel weights along the scan planes 120.c and 120.d. If the scan planes are parallel but non-uniformly spaced, the pixel weighting can vary from one scan plane to another to compensate for the non-uniform voxel sampling density from plane to plane. Trans-thoracic parallel scanning of the chambers of the heart is not easily performed due to the proximity of the rib cage, however, a transducer probe for scanning the heart from the esophagus with a plurality of transversely oriented parallel planes is described in U.S. Pat. No. 5,295,486.

Figure 6B:
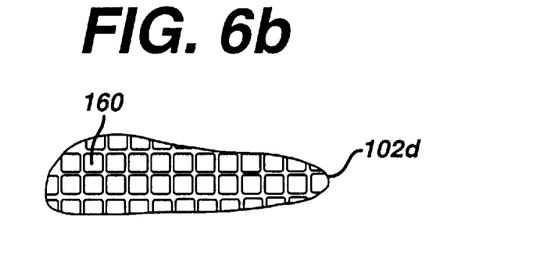
Figure 6C:
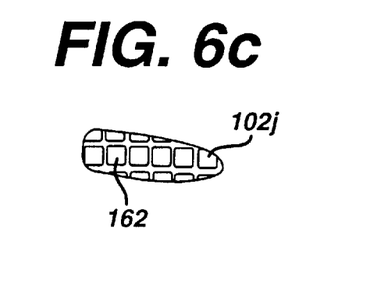

FIGS. 6b and 6c illustrate cross-sections 102d and 102j of the left ventricle blood pool of scan planes 120.d and 120.j, respectively. Since the entire blood pool is roughly cylindrical, more outwardly disposed scan planes will cut through and show ever smaller blood pool areas, as FIG. 6b and FIG. 6c demonstrate. The pixels 160 and 162 of the respective areas are uniformly weighted since the scan planes in the example are in parallel and uniformly spaced, and the weighted pixels of all of the blood pool areas of the scan planes are integrated or summed to determine a measure of the blood pool volume. As before, two sets of scan planes, one acquired at peak systole and the other acquired at end diastole, are acquired, the volumes at the two heart phases determined, then used to compute left ventricular ejection fraction.

It will be apparent to one skilled in the art that a number of refinements will aid the cardiac analysis of the present invention. For instance, assumptions as to the terminus of the top of the heart chamber and the mitral valve annulus may be employed to define the extent of the blood pool. Such delineation of the blood pool boundary may be done by manually drawing the border of the chamber with an image cursor, or by automated border tracing, or by automated computation of a "dam" defining the extent of the heart chamber. The assumptions inherent in such delineation techniques should not significantly affect the accuracy of the ejection fraction calculation, as the assumption will affect both the numerator and the denominator of the ratio.

Other variations from the described embodiments will be apparent to those skilled in the art and are within the scope of the present invention. While power Doppler imaging is the preferred technique for detecting blood flow in the heart due to its relatively high sensitivity, other Doppler techniques may be used, including Doppler velocity detection. Pulse to pulse subtraction as described in U.S. Pat. (appl. Ser. No. 08/655,394) may also be employed for detection of the endocardial border of the heart chamber rather than the bloodflow contained within the chamber. A number of spatially distinct scan planes of the chamber border are acquired, then pixels or segments of the border weighted in accordance with the density with which areas of the endocardial wall are sampled, the inter-plane spacing at the heart wall. Accumulating these weighted values will also provide a measure of the heart chamber volume, and such measures can be used to compute ejection fraction as described above.

It will also be appreciated that the techniques of the present invention may be enhanced through the use of ultrasonic contrast agents, enabling high sensitivity contrast agent detection within the heart chambers as described in U.S. Pat. No. 5,456,257 or by ultrasonic Doppler techniques. Harmonic contrast agents are especially advantageous, as they will afford good echo sensitivity even under the low flow conditions often present at end diastole and peak systole.

It will be appreciated that the volume measurement technique of the present invention may be used to measure the volume of other chambers of the heart and can be extended to measure the volume of any fluid filled vessel or organ of the body.

What is claimed is:

1. A method for using an ultrasonic diagnostic imaging system for measuring the volume of a fluid filled vessel or organ of the body such as a chamber of the heart, comprising the steps of:

scanning a chamber of the heart, vessel or organ in three dimensions by an ultrasonic technique which produces preferentially segmented samples of the blood pool of the chamber;

storing ultrasonic samples of a plurality of spatially distinct scan planes containing ultrasonic data of the blood pool of the chamber;

combining said ultrasonic data of said blood pool by summation or integration to develop a measure of the volume of said chamber; and displaying cardiac diagnostic information derived from said measure.

2. The method of claim 1, wherein said ultrasonic technique which produces preferentially segmented samples of the blood pool comprises a Doppler technique and wherein said ultrasonic data comprises ultrasonic Doppler data.

3. The method of claim 2, wherein said ultrasonic Doppler data comprises power Doppler data.

4. The method of claim 1, further comprising the step of weighting the ultrasonic data of a scan plane in accordance with the sampling density of the chamber afforded by said segmented samples of the blood pool.

5. The method of claim 4, wherein said weighting step comprises weighting the ultrasonic data of a scan plane in accordance with the inter-plane spacing of said scan planes.

6. The method of claim 1, wherein said ultrasonic data comprises image pixel data, and wherein said weighting step further comprises weighting the pixel data in accordance with the sampling density of the chamber blood pool afforded by said ultrasonic data.

7. The method of claim 6, wherein said weighting step comprises weighting the pixel data of a scan plane in accordance with the inter-plane spacing of said scan planes.

8. The method of claim 1, wherein said scanning step further comprises scanning the heart at a desired phase of the heart cycle.

9. The method of claim 8, wherein said segmented samples of the blood pool are acquired at substantially the same phase of the heart cycle.

10. The method of claim 9, wherein said storing step comprises storing two groups of segmented samples of the blood pool, each acquired at a different phase of the heart cycle; wherein said combining step comprises developing a measure of the volume of a chamber from each of said groups of segmented samples; and said displaying step further includes computing ejection fraction from said volume measures.

11. The method of claim 1, wherein said displaying step further comprises computing ejection fraction from said volume measurement.

12. The method of claim 1, wherein said ultrasonic technique which produces preferentially segmented samples of the blood pool comprises an ultrasonic contrast agent procedure wherein the blood pool contains a contrast agent.

13. The method of claim 12, wherein said ultrasonic contrast agent comprises a harmonic contrast agent.

14. The method of claim 13, wherein said storing step comprises storing two groups of segmented samples of the blood pool, each acquired at a different phase of the heart cycle; wherein said combining step comprises developing a measure of the volume of the chamber from each of said groups of segmented samples; and said displaying step further includes computing ejection fraction from said volume measures.

15. An ultrasonic diagnostic imaging system for measuring the volume of a chamber of the heart, comprising:

an ultrasonic transducer probe for acquiring ultrasonic data of the heart in three dimensions at different scan plane orientations;

means for storing a plurality of spatially distinct scan planes containing ultrasonic data of a chamber of the heart;

means for delineating endocardial border data of said chamber in said scan planes;

means for weighting said delineated endocardial border data in accordance with the sampling density of the endocardium afforded by said scan planes; and means for combining said weighted endocardial border data to develop a measure of the volume of said chamber.

16. The ultrasonic diagnostic imaging system of claim 15, wherein said means for weighting comprises means for weighting the delineated endocardial border data of a scan plane in accordance with the interplane spacing of said scan planes.

17. An ultrasonic diagnostic imaging system for measuring the volume of a vessel or organ of the body, comprising:

an ultrasonic transducer probe for acquiring ultrasonic data of the vessel or organ in three dimensions at different scan plane orientations;

a device for storing a plurality of spatially distinct scan planes containing ultrasonic data of said vessel or organ;

a circuit for weighting the ultrasonic data of a scan plane in accordance with the sampling density of the interior of said vessel or organ afforded by said scan planes; and a processor for combining said weighted ultrasonic data from said scan planes to develop a measure of the volume of said vessel or organ.

18. The ultrasonic diagnostic imaging system of claim 17, wherein said ultrasonic data comprises ultrasonic Doppler data.

19. The ultrasonic diagnostic imaging system of claim 18, wherein said ultrasonic Doppler data comprises ultrasonic power Doppler data.

20. A method for measuring the volume of a chamber of a heart containing an ultrasonic contrast agent comprising the steps of:

acquiring ultrasonic data from the heart chamber in three dimensions at different scan plane orientations;

storing a plurality of spatially distinct scan planes containing ultrasonic data derived from ultrasonic signals received from contrast agent in said chamber of the heart; and combining said ultrasonic data from said scan planes to develop a measure of the volume of said chamber of the heart.

21. The method of claim 20, wherein said ultrasonic contrast agent comprises a harmonic ultrasonic contrast agent.

22. An ultrasonic diagnostic imaging system for measuring the volume of a chamber of the heart, comprising:

an ultrasonic transducer probe for acquiring ultrasonic data of the heart at different scan plane orientations which are parallel to one another;

means for storing a plurality of spatially distinct scan planes containing ultrasonic data of a chamber of the heart; and means for combining said ultrasonic data from said scan planes to develop a measure of the volume of said chamber of the heart; further comprising means for weighting said ultrasonic data of said scan planes in accordance with the separation of adjacent scan planes; and wherein said means for combining comprises means for combining said weighted ultrasonic data.

23. An ultrasonic diagnostic imaging system for measuring the volume of a chamber of the heart, comprising:

an ultrasonic transducer probe for acquiring ultrasonic data of the heart at different scan plane orientations which share a common scanline orientation;

means for storing a Plurality of spatially distinct scan planes containing ultrasonic data of a chamber of the heart; and a processor for combining said ultrasonic data from said scan planes to develop a measure of the volume of said chamber of the heart; further comprising a weighting circuit for weighting said ultrasonic data of said scan planes in accordance with the separation of adjacent scan planes; and wherein said processor comprises means for combining said weighted ultrasonic data.

24. An ultrasonic diagnostic imaging system for measuring the volume of a chamber of the heart, comprising:

an ultrasonic transducer probe for acquiring ultrasonic data of the heart at different scan plane orientations which are angularly inclined with respect to one another;

means for storing a plurality of spatially distinct scan planes containing ultrasonic data of the interior volume of a chamber of the heart; and a processor for combining said ultrasonic data of the interior volume of said chamber from said scan planes to develop a measure of the volume of said chamber of the heart; further comprising a weighting circuit for weighting said ultrasonic data of said scan planes in accordance with the separation of adjacent scan planes; and wherein said processor comprises means for combining said weighted ultrasonic data.

* * * * *